United States Patent [19]
Abidin et al.

[11] Patent Number: 5,545,175
[45] Date of Patent: *Aug. 13, 1996

[54] DISPOSABLE QUARDED FINGER SCALPEL FOR INSERTING A LINE IN A PATENT AND LOCK OFF THEREFOR

[75] Inventors: Micheal R. Abidin, Tampa, Fla.; Steven P. Lehmbeck, Baltimore, Md.

[73] Assignee: Leonard Bloom, Towson, Md.

[*] Notice: The term of this patent shall not extend beyond the expiration date of Pat. No. 5,370,654.

[21] Appl. No.: 287,123

[22] Filed: Aug. 8, 1994

Related U.S. Application Data

[63] Continuation-in-part of Ser. No. 079,985, Jun. 18, 1993, Pat. No. 5,370,654.

[51] Int. Cl.$^6$ ............................................. A61B 17/32
[52] U.S. Cl. ........................ 606/182; 606/167; 606/185; 30/162
[58] Field of Search ..................................... 606/182, 167, 606/185, 172, 181, 189, 170; 30/162; 70/158–161, 57, 58, 61

[56] References Cited

U.S. PATENT DOCUMENTS

| | | | |
|---|---|---|---|
| 2,753,105 | 7/1956 | Werner et al. | 229/51 |
| 3,863,339 | 2/1975 | Reaney et al. | 30/162 |
| 3,895,441 | 7/1975 | Horak | 30/162 |
| 3,906,626 | 9/1975 | Riuli | 30/162 |
| 4,414,974 | 11/1983 | Dotson et al. | |
| 4,601,710 | 7/1986 | Moll | 604/165 |
| 4,760,848 | 8/1988 | Hasson. | |
| 4,902,280 | 2/1990 | Lander | 604/165 |
| 4,955,887 | 9/1990 | Zirm | 606/107 |
| 5,066,288 | 11/1991 | Deniega et al. | 604/274 |
| 5,139,507 | 8/1992 | Dolgin et al. | 606/167 |
| 5,208,983 | 5/1993 | Masse | 30/340 |
| 5,211,652 | 5/1993 | Derbyshire | 606/182 |
| 5,231,993 | 8/1993 | Haber et al. | 128/770 |
| 5,370,654 | 12/1994 | Abidin et al. | 606/182 |

FOREIGN PATENT DOCUMENTS 3526821  2/1987  Germany.

*Primary Examiner*—Tamara L. Graysay
*Attorney, Agent, or Firm*—Leonard Bloom

[57] ABSTRACT

A guarded finger scalpel is squeezed between the thumb and forefinger to advance a blade out of an opening. The blade is used to make an incision in the patient's skin, thereby facilitating insertion of a catheter and its line in a patient. Thereafter, the manual pressure is released, and the blade is automatically retracted. This prevents inadvertent or accidental nicks or cuts and hence eliminates or, at least, substantially reduces the exposure to the AIDS virus or other infectious diseases. A lock-off means is employed, subsequent to the surgical procedure, to prevent further blade exposure during clean-up and disposal.

14 Claims, 13 Drawing Sheets

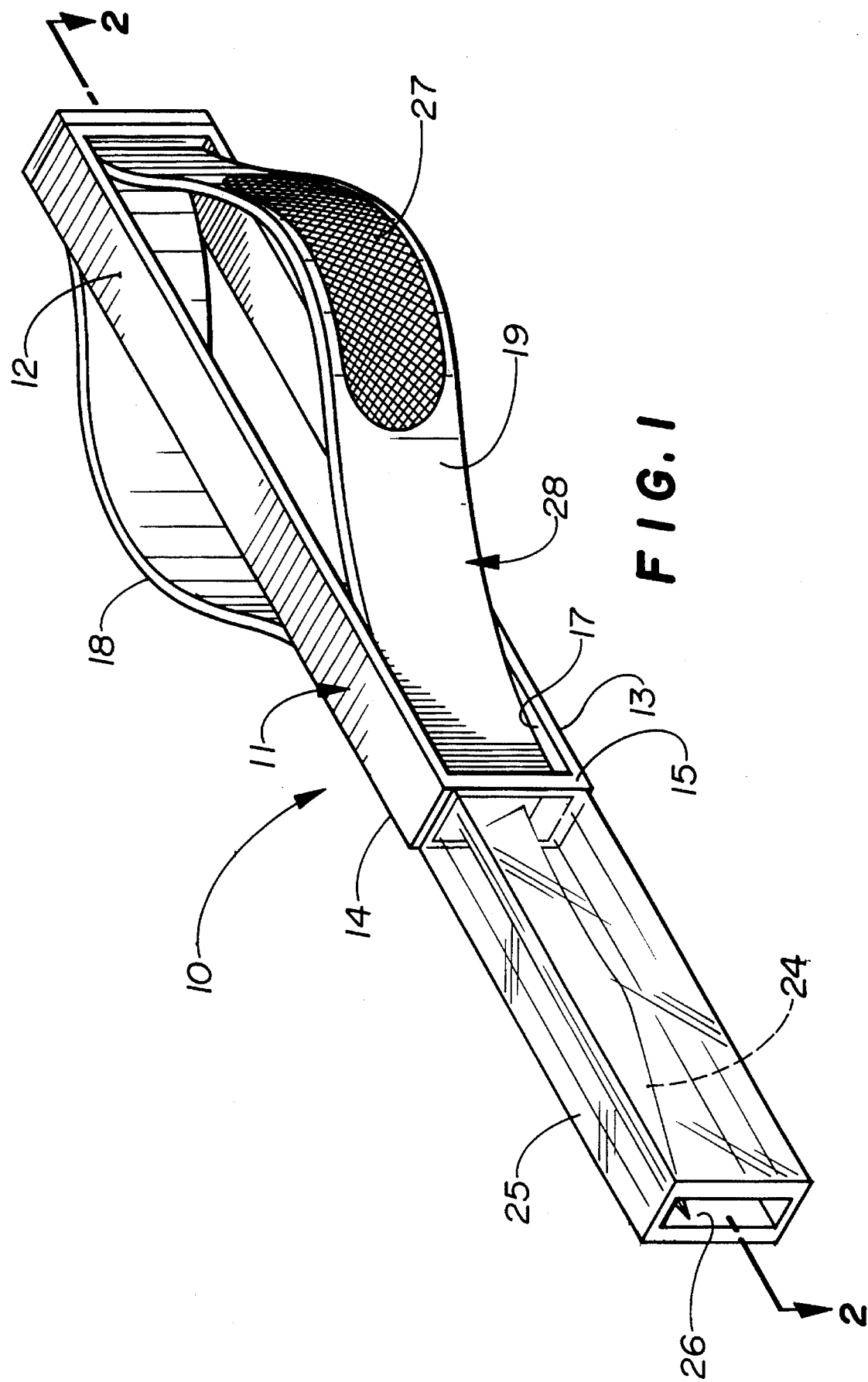

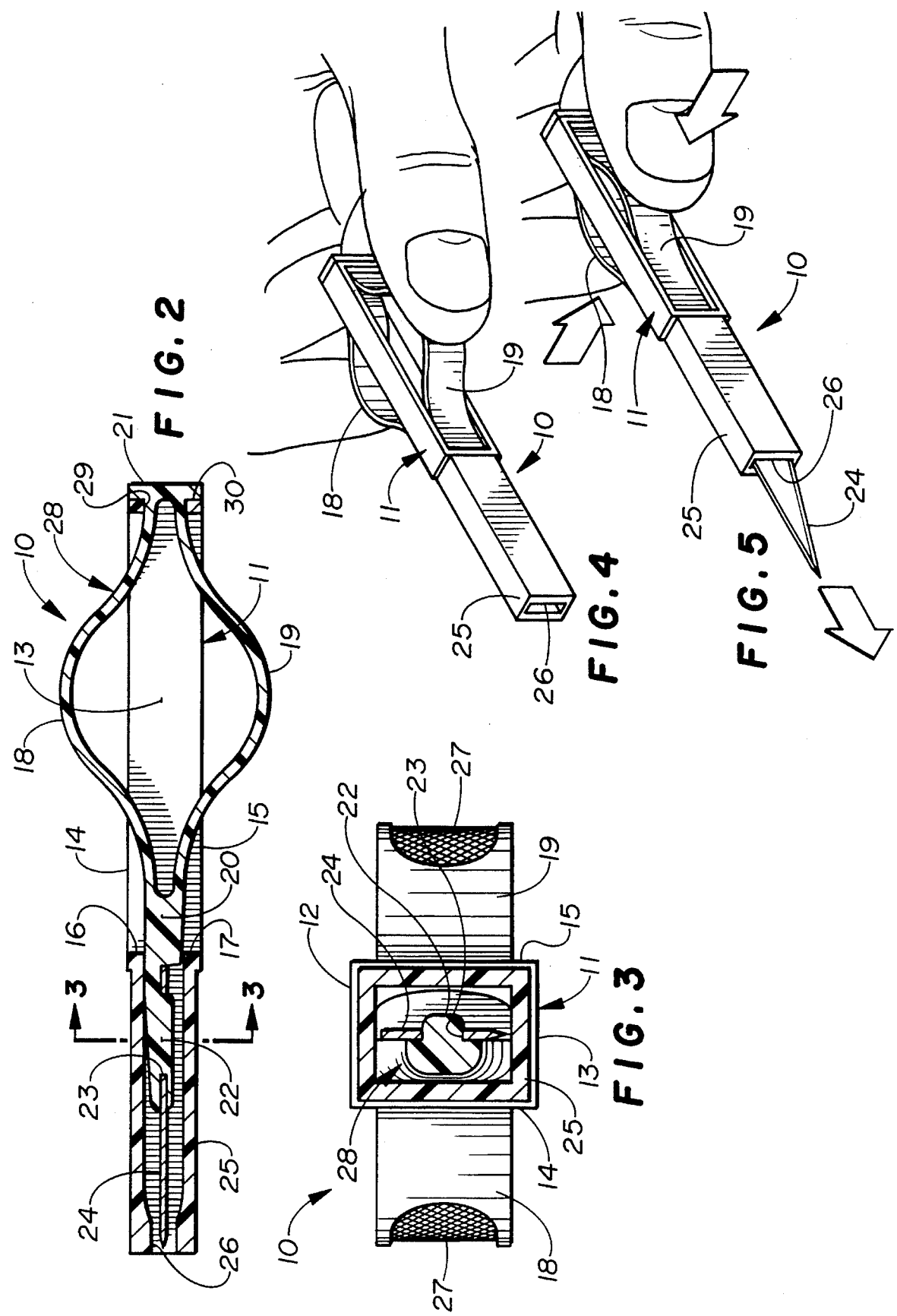

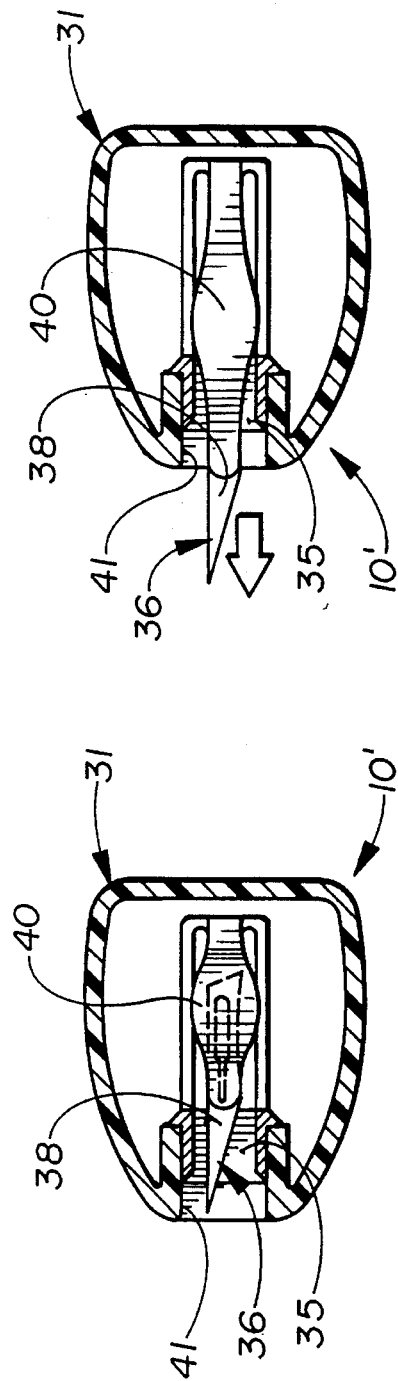
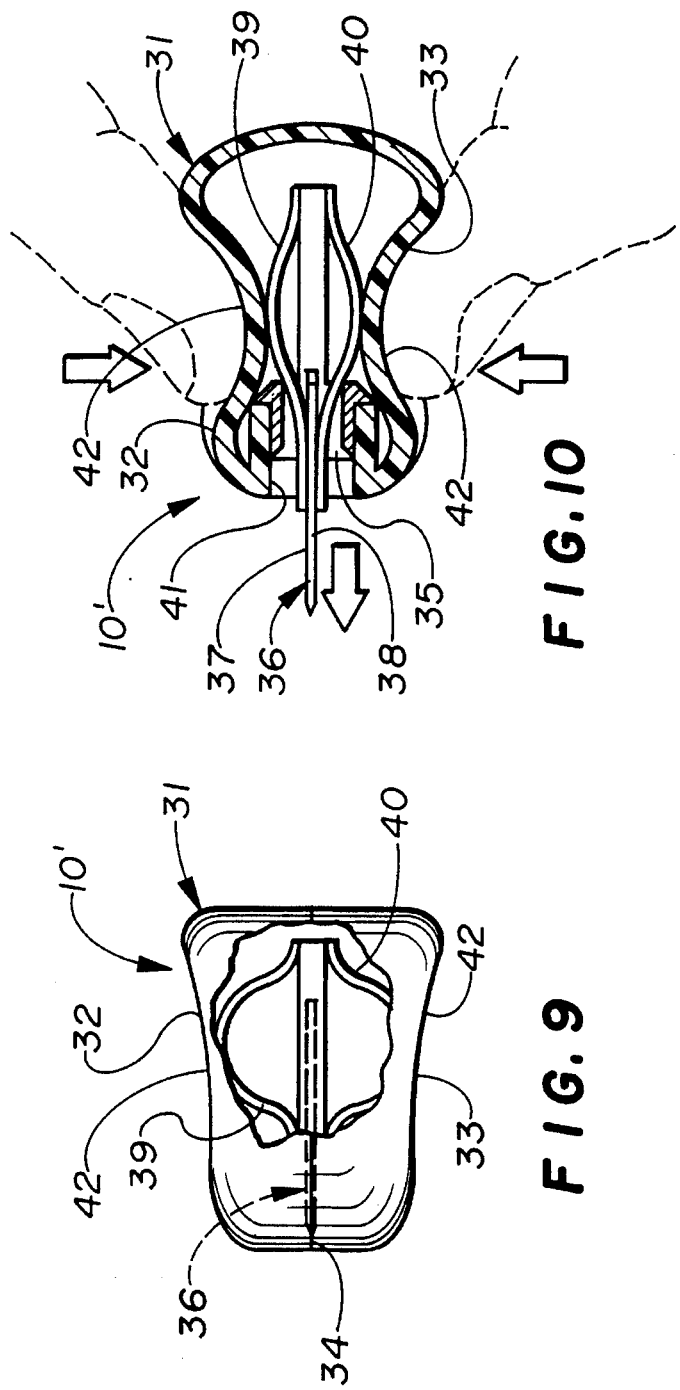
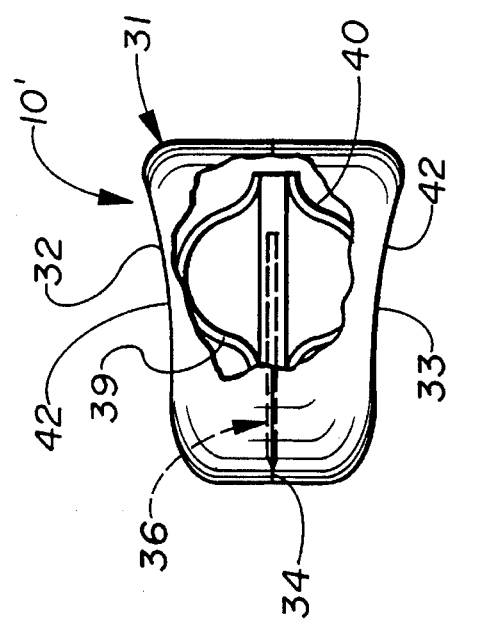

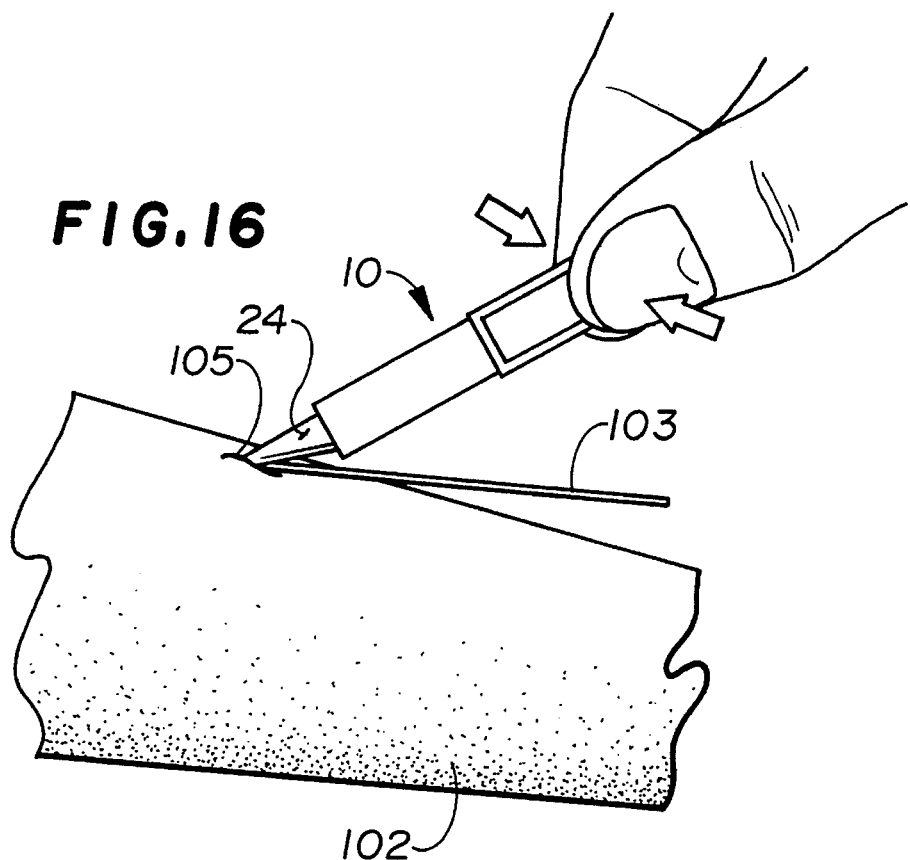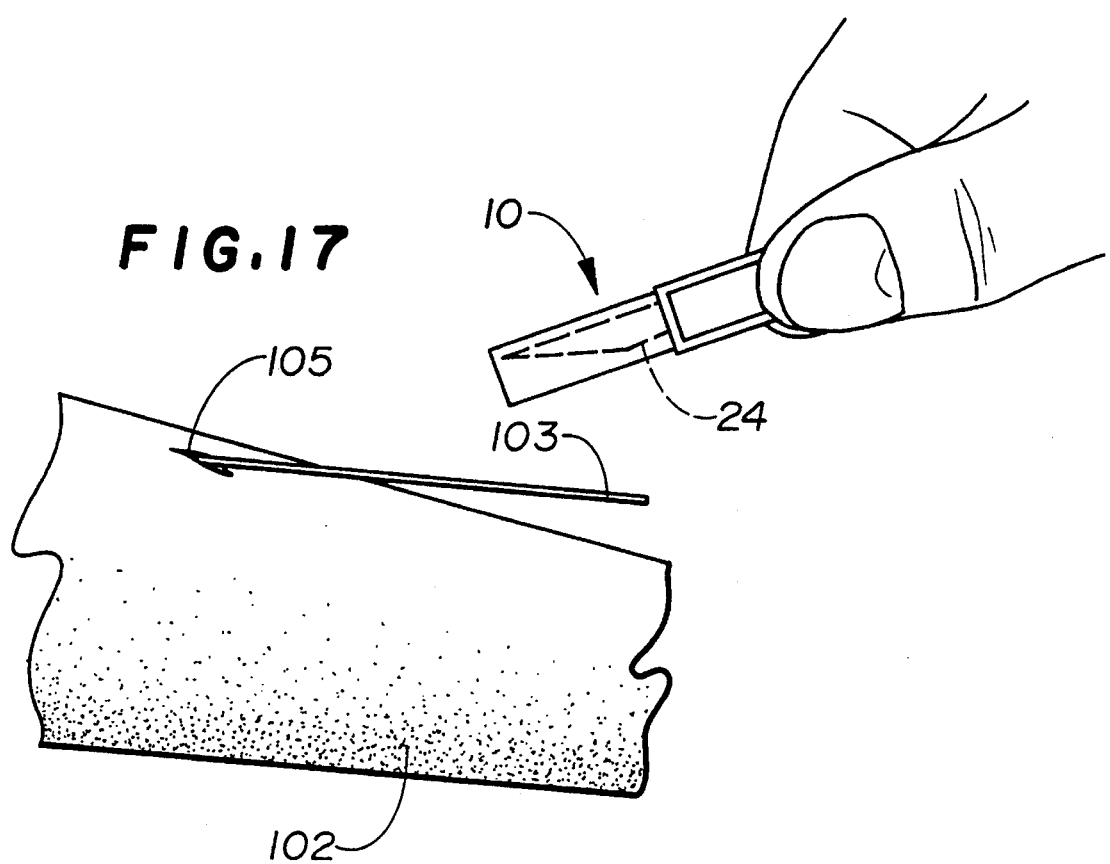

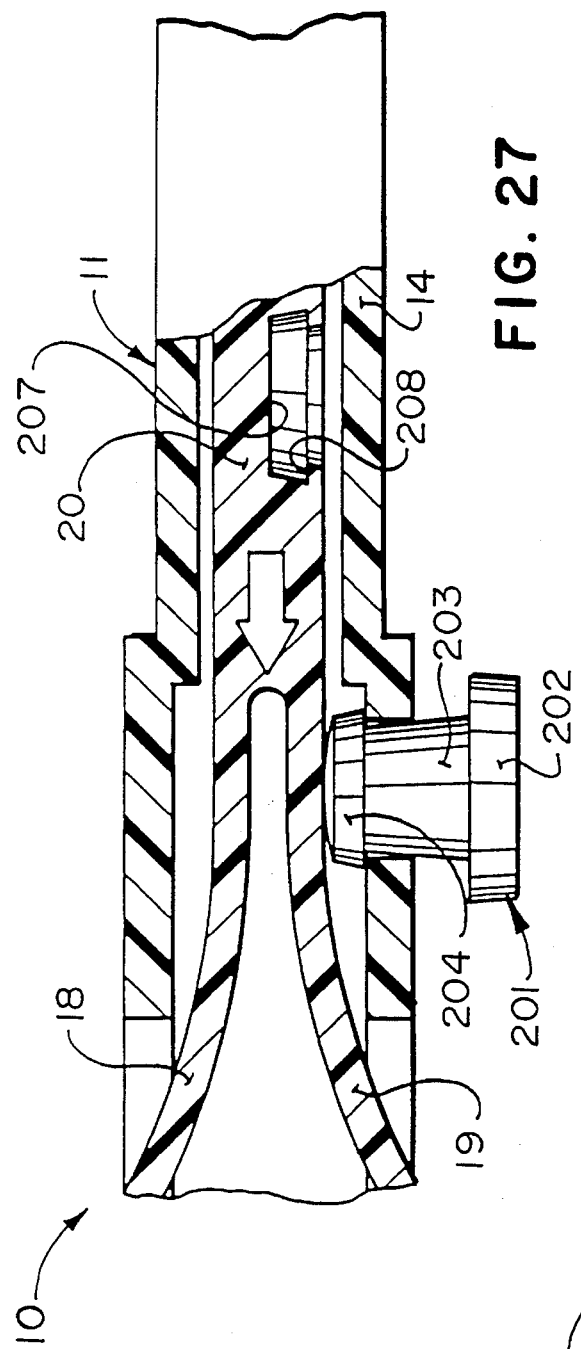
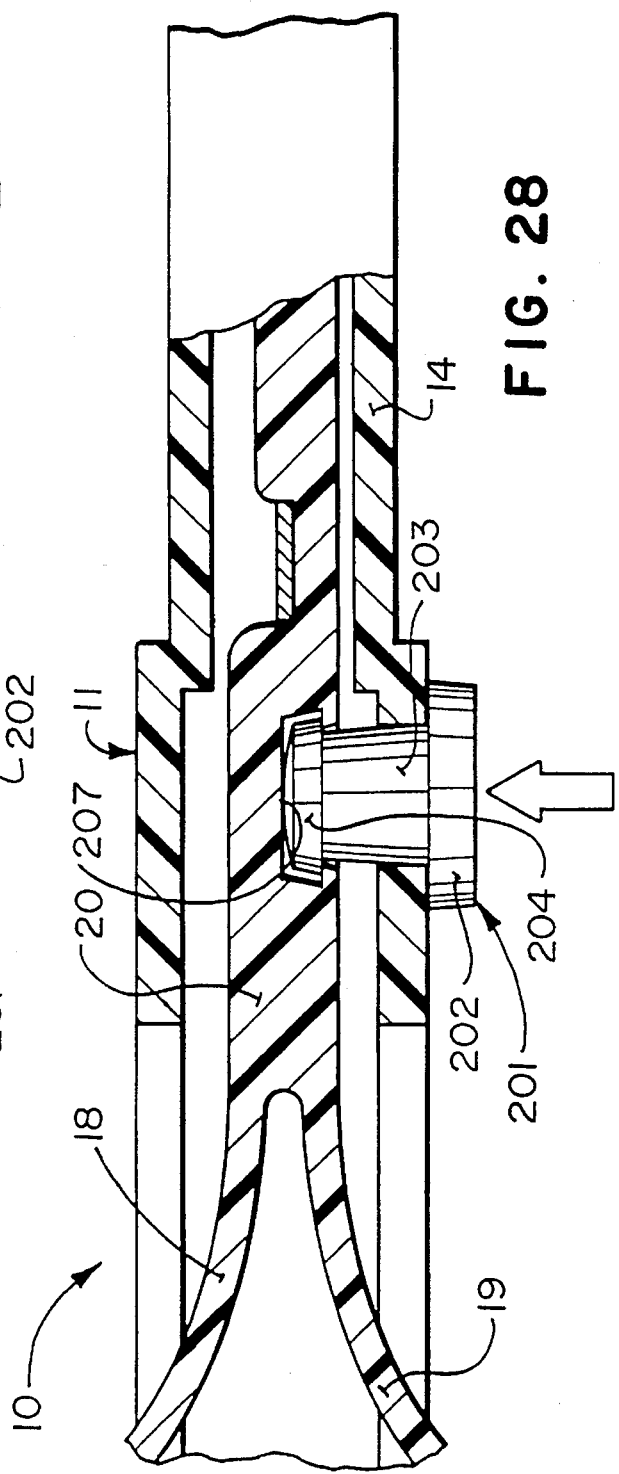
FIG. 27
FIG. 28

DISPOSABLE QUARDED FINGER SCALPEL FOR INSERTING A LINE IN A PATENT AND LOCK OFF THEREFOR

CROSS-REFERENCE TO RELATED APPLICATION

The present invention constitutes a continuation-in-part of application Ser. No. 08/079,985 filed Jun. 18, 1993, now U.S. Pat. No. 5,370,654, the disclosure of which is incorporated herein in its entirety.

FIELD OF THE INVENTION

The present invention relates to a finger scalpel for making a small cut or incision in a patient's skin to facilitate insertion of a catheter, and more particularly, to a guarded finger scalpel to prevent inadvertent or accidental nicks or cuts incurred by any of the health care providers involved in using the finger scalpel or in the subsequent clean up and disposal thereof.

BACKGROUND OF THE INVENTION

In the process of establishing a line in a patient (as for example, during a heart bypass operation) a catheter is inserted into the patient. The purpose of the catheter may be to position a sensor or other device within the patient or to inject a medication or a dye into the patient. In order to insert the catheter, it is first necessary to insert a guide wire through the patient's skin and to locate one of the patient's veins (or other vessel, body cavity or organ). The guide wire comprises a flexible cable which is inserted through a puncture in the patient's skin, the puncture being made by a needle. Since the puncture is relatively small compared to the catheter, and since the catheter is relatively soft and flexible and may bend, it is necessary to enlarge the puncture by making a small incision or cut substantially at the puncture or adjacent thereto.

This relatively small cut is made by a finger scalpel. The finger scalpel comprises a surgical blade attached to a small plastic handle that is grasped, typically, between the surgeon's thumb and forefinger.

After the cut is made, the surgeon merely drops the finger scalpel on the tray or on the patient's gurney. Since the blade is exposed (and usually contains blood or bodily fluids) this is a hazardous situation. The danger occurs in using the finger scalpel, or in cleaning up the operating room or patient's room, or in subsequent disposal of the used scalpel.

Accidental or inadvertent contact with the unguarded finger scalpel often results in the health care provider being nicked or cut, and exposure with the blood or bodily fluids on the blade may result in the health care provider sero-converting and thus becoming infected with Hepatitis B or the deadly HIV ("AIDS") virus.

Even if an infection does not occur, repeated testing and observation is necessary whenever a known AIDS patient is involved. This testing is worrisome, inconvenient and costly.

Conversely, there is also a risk to the patient in the event the surgeon or other health care provider is infected with AIDS or any contagious disease.

While no specific data is available with regard to finger scalpels, the risk is at least comparable to the problems associated with needle sticks. A study was made by the Needle Stick Surveillance Group of the C.D.C. (Centers for Disease Control). Out of 3,978 needle sticks from patients known to be HIV positive, 13 health care workers became infected—roughly 1 out of 300. Thus, from a single needle stick while treating an AIDS patient in an operating room or other environment, the chances are roughly 1 out of 300 that the surgeon, nurse or other individual health care provider will sero-convert and become HIV positive.

SUMMARY OF THE INVENTION

Accordingly, it is an object of the present invention to provide a guarded finger scalpel which substantially eliminates inadvertent or accidental contact with the blade, thereby preventing the spread of infectious diseases.

It is another object of the present invention to provide a guarded finger scalpel having a retracted blade; such that when the scalpel is grasped or squeezed between the surgeon's thumb and forefinger, the blade is advanced and exposed for use; and such that when the scalpel is released, the blade is automatically retracted to its original position and is thereby guarded against accidental or inadvertent contact.

It is a further object of the present invention to provide a lock-off means to prevent movement of the blade relative to the guard following use of the guarded finger scalpel during a surgical procedure, thereby preventing accidental nicks or cuts during clean-up.

In accordance with the teachings of the present invention, the guarded finger scalpel includes a body normally grasped between a surgeon's thumb and forefinger. This body includes a blade guide means having a forward portion provided with an opening formed therein. A blade is slidably guided within the blade guide means and has respective sides. A pair of spring arms are connected to the blade and extend laterally of the blade on respective sides thereof. These spring arms are manually squeezed towards each other, thereby advancing the blade outwardly through the opening in the forward portion of the blade guide means in the body. Conversely, the blade is automatically retracted within the body when the spring arms are released to return to their original position.

In one embodiment, the body comprises a substantially rectangular frame having top and bottom walls and side portions provided with respective openings formed therein; the spring arms extend laterally through the openings, respectively, and are confined by the top and bottom walls of the frame.

In another embodiment, the body is substantially resilient and has respective side walls, and the respective spring arms are confined within the resilient body and engage the respective side walls thereof. With this arrangement, the respective side walls of the resilient body may be squeezed together to thereby deflect the spring arms towards each other.

Viewed in another aspect, the present invention constitutes an improvement in the method of inserting a line in a patient, wherein a needle is used to make a puncture in the patient's skin to locate a vein (or other vessel, cavity or organ) in the patient. A guide wire is inserted through the needle and through the puncture and into the patient, and the needle is removed. A catheter is inserted over the guide wire and into the patient, the wire being removed when the catheter is installed. The improvement includes the steps of providing a guarded finger scalpel having a covered blade, manually grasping the guarded finger scalpel and advancing the blade, making a cut in the patient's skin substantially at the puncture before the catheter is inserted over the guide wire, thereby facilitating insertion of the catheter, and automatically retracting the blade within the guarded finger scalpel, thereby preventing nicks or cuts due to accidental or inadvertent contact with the scalpel during use, clean-up or disposal thereof.

Viewed in still another aspect, the present invention provides a finger scalpel for use by a surgeon in installing a line in a patient in a hospital, wherein the finger scalpel is part of a disposable kit, and wherein the finger scalpel includes a body normally intended to be grasped between the surgeon's thumb and forefinger, the body having a blade mounted thereon. In accordance with the teachings of the present invention, a guard is provided on the body. The guard has a normal position covering the blade and preventing accidental contact therewith. A resilient means maintains the guard in the normal position thereof, such that the resilient means may be manually opposed as the finger scalpel is grasped by the surgeon, thereby exposing the blade relative to the guard. A lock-off means independent of the resilient means is provided. The lock-off means is operative in the normal position of the guard and prevents blade exposure, such that the clean-up personnel in the hospital are protected against nicks or cuts during disposal of the kit.

In a preferred embodiment, the lock-off means includes a lock-off button carried transversely by one of the side walls of the frame.

The inner member within the frame has a pocket formed therein. The lock-off button may be pushed inwardly of the frame and received within the pocket in the inner member, thereby locking the inner member to the frame and preventing relative sliding movement therebetween.

In another embodiment, the lock-off button is carried on a depressible tang formed on the one side wall of the frame.

These and other objects of the present invention will become apparent from a reading of the following specification taken in conjunction with the enclosed drawings.

BRIEF DESCRIPTION OF THE DRAWINGS

FIG. 1 is a perspective view of one embodiment of the guarded finger scalpel of the present invention.

FIG. 2 is a cross-sectional view thereof, taken along the lines 2—2 of FIG. 1, and showing the respective spring arms connected to the blade, and further showing the spring arms extending through respective openings formed in the side portions of the rectangular frame.

FIG. 3 is a cross-sectional view thereof, taken along the lines 3—3 of FIG. 2, showing the blade within the blade guide means.

FIG. 4 is a pictorial view showing the guarded finger scalpel being grasped by the surgeon.

FIG. 5 is a further pictorial view, corresponding substantially to FIG. 4, but showing the respective spring arms of the guarded finger scalpel being squeezed between the surgeon's thumb and forefinger to advance the blade out of the blade guide means.

FIG. 7 is a side elevation of a second embodiment of the guarded finger scalpel of the present invention with certain parts thereof broken away and sectioned to show the blade fully retracted within the body of the guarded finger scalpel.

FIG. 8 corresponds substantially to FIG. 7, but shows the resilient body of the guarded finger scalpel being squeezed between the surgeon's thumb and forefinger to advance the blade through an opening in the body of the guarded finger scalpel.

FIG. 9 is a top plan view corresponding to FIG. 7, with certain parts broken away, and showing a pair of spring arms connected between respective side portions of the blade and the resilient body of the guarded finger scalpel.

FIG. 10 is a further top plan view with certain parts broken away and sectioned, corresponding substantially to FIG. 9, but showing the body squeezed to deflect the spring arms to extend the blade.

FIGS. 11—21 are pictorial views showing the sequence of using the guarded finger scalpel to make a cut (or cuts) in the patient to enable a catheter to be inserted into the patient.

FIG. 11 shows the needle making a puncture in the patient's skin to locate a vein, and further shows (in exploded relationship thereto) a flexible guide wire about to be inserted into the needle.

FIG. 12 shows the guide wire inserted into the vein, and further shows the needle being withdrawn therefrom.

FIG. 13 is a cross-sectional view thereof, taken along the lines 13—13 of FIG. 12, and drawn to an enlarged scale.

FIG. 14 shows the scalpel being picked up by the surgeon.

FIG. 15 shows the resilient body of the scalpel being squeezed between the surgeon's thumb and forefinger to thereby advance the blade out of the body of the guarded finger scalpel.

FIG. 16 shows the blade being used to make a small cut (or cuts) at the puncture in the patient's skin or substantially adjacent thereto, thereby enlarging the puncture to facilitate insertion of the catheter.

FIG. 17 shows the guarded finger scalpel being released to automatically retract the blade.

FIG. 18 shows the catheter being inserted over the guide wire, concentrically thereof.

FIG. 19 shows the catheter being inserted through the cut and into the patient's vein.

FIG. 20 is a cross-sectional view thereof, taken along the lines 20—20 of FIG. 19, and drawn to an enlarged scale.

FIG. 21 is a further cross-sectional view, corresponding substantially to FIG. 20, but showing the guide wire being withdrawn from the catheter in the patient's vein.

FIG. 27 is a longitudinal sectional view, taken along the lines 27—27 of FIG. 23 and drawn to an enlarged scale, and showing the inner member being retracted into its normal position on the frame.

FIG. 28 is a further longitudinal sectional view, corresponding substantially to FIG. 27, but showing the inner member fully retracted within the frame and the lock-off button pushed inwardly and received within the pocket on the inner member, thereby locking the inner member to the frame and preventing further movement of the inner member relative to the frame.

GENERAL DESCRIPTION OF THE PREFERRED EMBODIMENT

Figure 6:
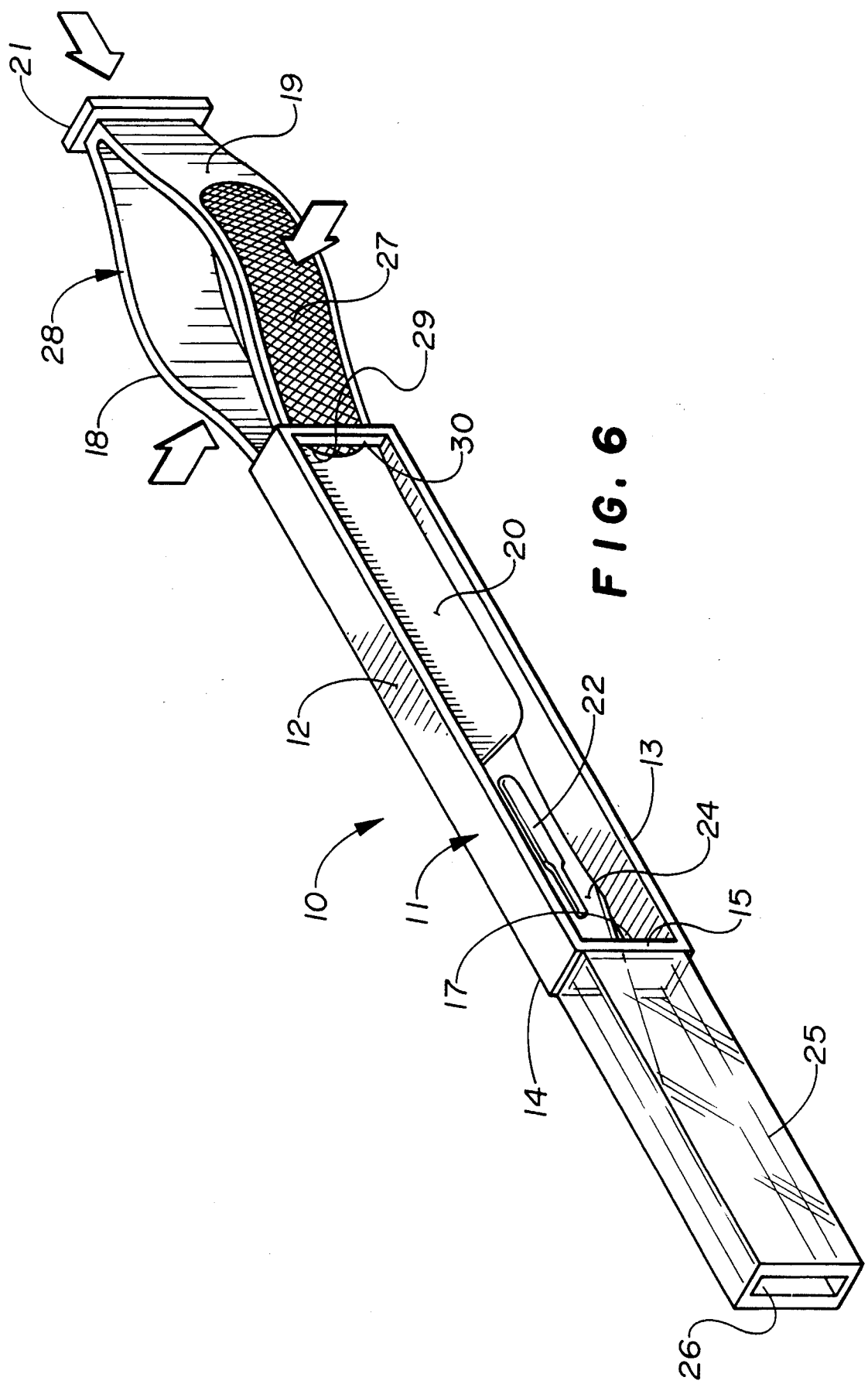
FIG. 6 is an exploded perspective view, showing the assembly of the components of the guarded finger scalpel of FIG. 1.

With reference to FIGS. 1–3, the guarded finger scalpel 10 of the present invention includes a substantially rectangular frame 11 having a top wall 12, a bottom wall 13 and respective side portions 14 and 15 having openings 16 and 17, respectively, formed therein. A pair of spring arms 18 and 19 (resilient means), respectively, are confined between the top wall 12 and the bottom wall 13 of the frame 11, being disposed rearwardly of the frame 11 as shown in FIG. 3, and extend laterally thereof through the openings 16 and 17, respectively.

These spring arms 18 and 19 are bifurcated and, preferably, are formed from a single plastic moldment (as shown more clearly in FIG. 2) and are joined together, first, at a forward portion 20 and, second, at a rearward cap 21. The forward portion 20 of the spring arms 18, 19 includes a longitudinally-extending lug 22 received within a longitudinal slotted opening 23 formed within a surgical blade 24. The lug 22 may be swaged over the blade 24 and secured thereto (as shown more clearly in FIGS. 2 and 3) by hot-staking or other production process.

The blade 24 is slidably guided within a blade guide means 25 having an opening 26. The blade guide means 25 constitutes a guard for the blade 24 and (in this embodiment) is substantially rectangular and is formed integrally with the frame 11, as for example, by a unitary plastic moldment. Preferably, the blade guide means 25 is transparent, so that the blade 24 is visible at all times (even when the blade 24 is normally confined therein).

The exposed faces of the laterally-extending spring arms are roughened, as at 27 in FIG. 1, to facilitate a manual grasping and manipulation of the guarded finger scalpel 10.

When the guarded finger scalpel 10 is thus grasped between the surgeon's thumb and forefinger (FIG. 4), the spring arms 18, 19 are squeezed together (FIG. 5) laterally inwardly of the frame 11 to thereby advance the blade 24 out of the opening 26.

Thus the blade 24 of the guarded finger scalpel 10 of the present invention is only exposed while a cut or cuts are being made, thereby substantially reducing (if not eliminating altogether) the risks associated with using a conventional unguarded finger scalpel, not only in the highly-stressed environment of an operating room or critical care unit, but also in the subsequent clean up and disposal of the overall kit including the scalpel.

With reference again to FIG. 2, and with further reference to FIG. 6, the blade 24 and the spring arms 18 and 19 with their rearward cap 21 constitutes a subassembly 28 or inner member nested within the frame 11. In the assembly of the guarded finger scalpel 10, the subassembly 28 is received through an opening 29 in a rear wall 30 of the frame 11. The spring arms 18 and 19 are squeezed together to clear the opening 30, and the spring arms 18, 19 are then released to enable the spring arms 18, 19 through the openings 16, 17 and laterally of the frame 11. The cap 21 is then seated against the rear wall 30 of the frame 11 and may be secured thereby by protrusions (not shown) or by ultrasonic welding, hot-staking or any suitable production process.

The guarded finger scalpel 10 comprises only three parts: the molded frame 11, the molded spring arms 18 and 19, and the metal blade 24, respectively. Accordingly, the guarded finger scalpel 10 facilitates high-volume low-cost automated manufacture.

An alternate embodiment 10' of the guarded finger scalpel of the present invention is illustrated in FIGS. 7–10. This guarded finger scalpel 10' has a resilient body 31, preferably of a suitable molded plastic material, and being relatively small and easy to handle and to orient. Preferably, the body 31 has complementary halves 32 and 33, respectively, joined together along a common longitudinal midplane 34 and suitably secured together, as for example, by ultrasonic welding.

A blade guide means or frame 35 is mounted within the resilient body 31, and a blade 36 is slidably guided within the frame 35. The blade 36 has respective sides 37 and 38; and a pair of spring arms 39 and 40, respectively, are connected between the sides 37, 38 and the resilient body 31.

As the resilient body 31 is squeezed between the surgeon's thumb and forefinger, as shown in FIGS. 8 and 10, the respective spring arms 39 and 40 deflect, that is, are compressed towards the frame 35; and as a result, the blade 36 is advanced forwardly out of an opening 41 formed in the body 31.

Conversely, when the finger pressure is released, the respective spring arms 39 and 40 return to their original position (FIGS. 7 and 9) and the blade 36 is again retracted within the body 31.

The sides of the resilient body are indented, as at 42, to facilitate manual manipulation of the guarded finger scalpel 10'.

Thus, with the guarded finger scalpels 10 and 10' of the present invention, the blades 24 and 36, respectively, are exposed only when making a cut or cuts in the patient's skin. Otherwise, the blades 24, 36 are covered at all times. Accordingly, the guarded finger scalpels 10 and 10' of the present invention protect against inadvertent or accidental nicks or cuts occasionally encountered by health care providers (such as surgeons, nurses, technicians, operating room assistants and clean-up personnel) and the serious health risks associated therewith.

The protection also extends to the patient (or patients) if the surgeon or other health care provider is infected with HIV (the deadly AIDS virus) or any other contagious disease. In the event an unguarded finger scalpel becomes contaminated by tainted blood from the surgeon or other health care provider, the disease may be inadvertently communicated to the patient.

The protection afforded by the guarded finger scalpels 10 and 10' of the present invention, and the benefits and advantages of its improved method, are illustrated in FIGS. 11–21.

Figure 11:
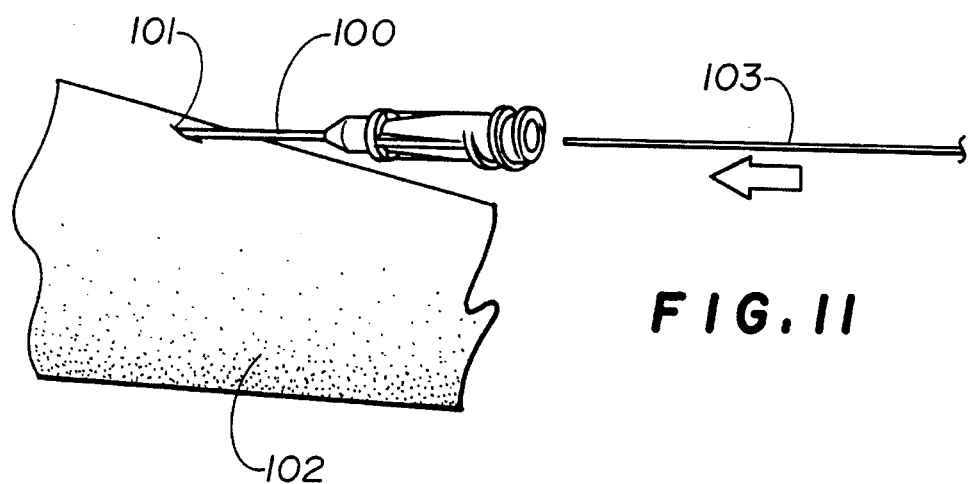
Figure 12:
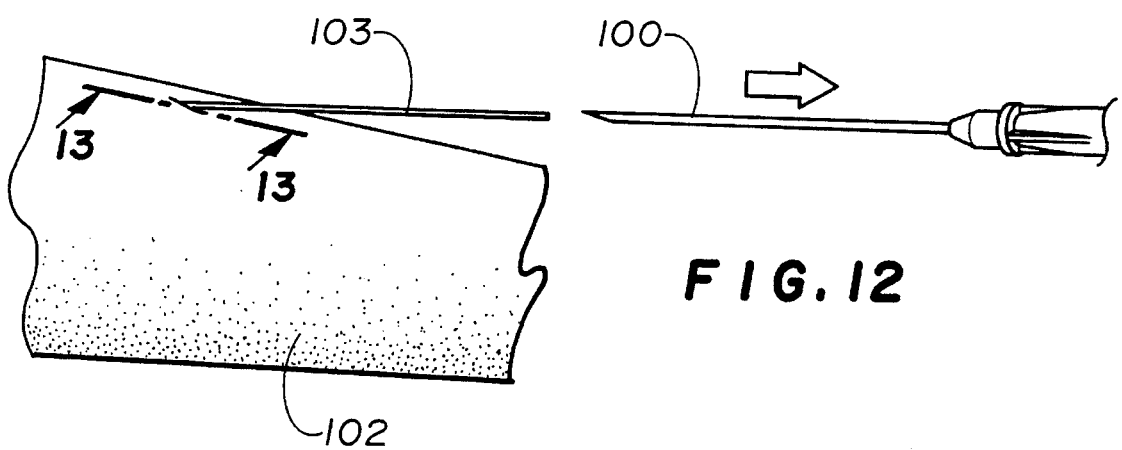
Figure 13:
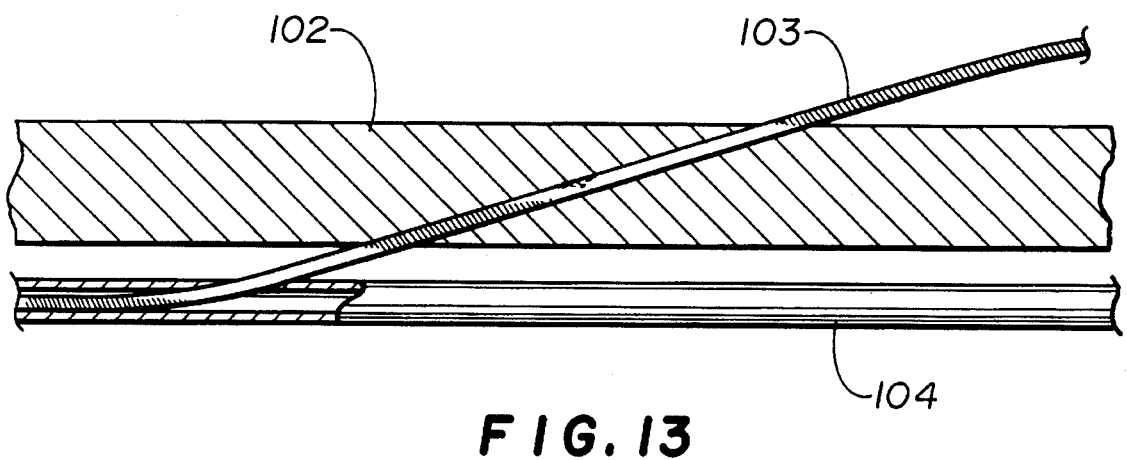
Figure 14:
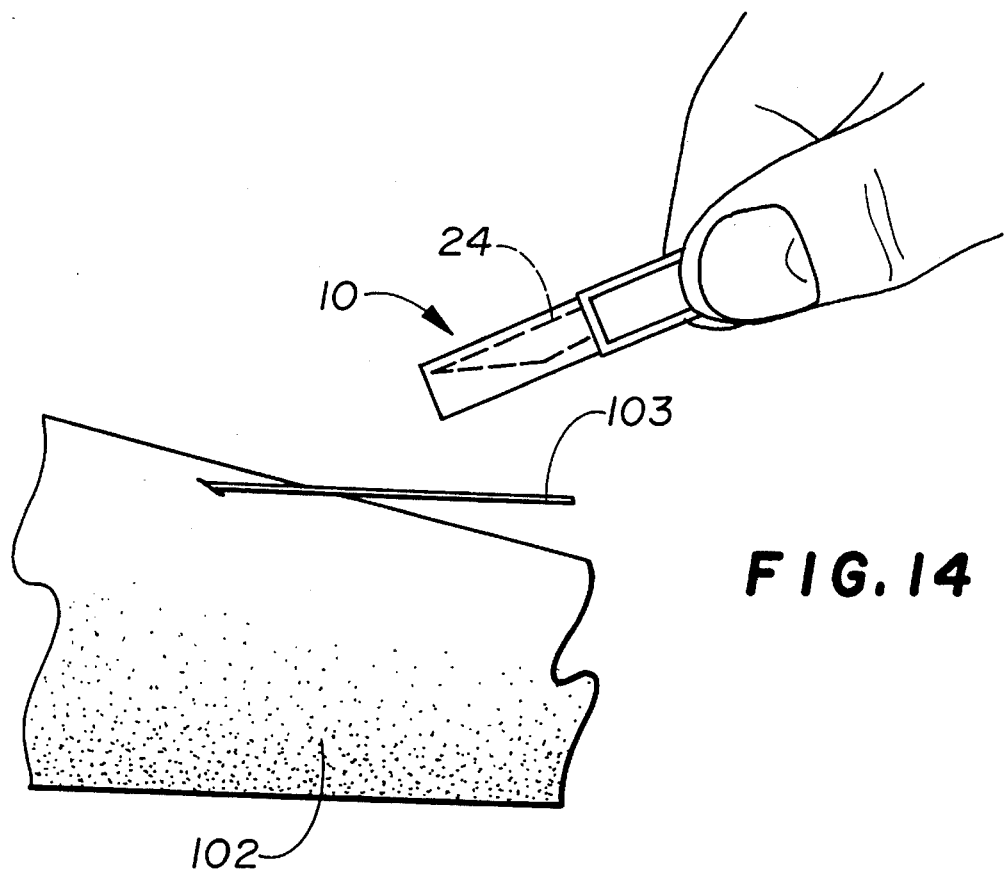

In FIG. 11, a needle 100 is used to make a puncture 101 in a patient's arm 102 to thereby locate a vein (for example). The needle 100 is an "introducer" needle. In some cases, it may be necessary to first use a smaller "starter" needle (now shown) to locate the patient's vein. Thereafter, a flexible guide wire 103 is inserted through the needle 100 and through the puncture 101 (FIG. 12) and into the vein 104 (FIG. 13). The needle 100 is then removed and the guide wire 103 remains in the lumen, that is, within the opening in the vein, artery or intestine of the patient.

Figure 15:
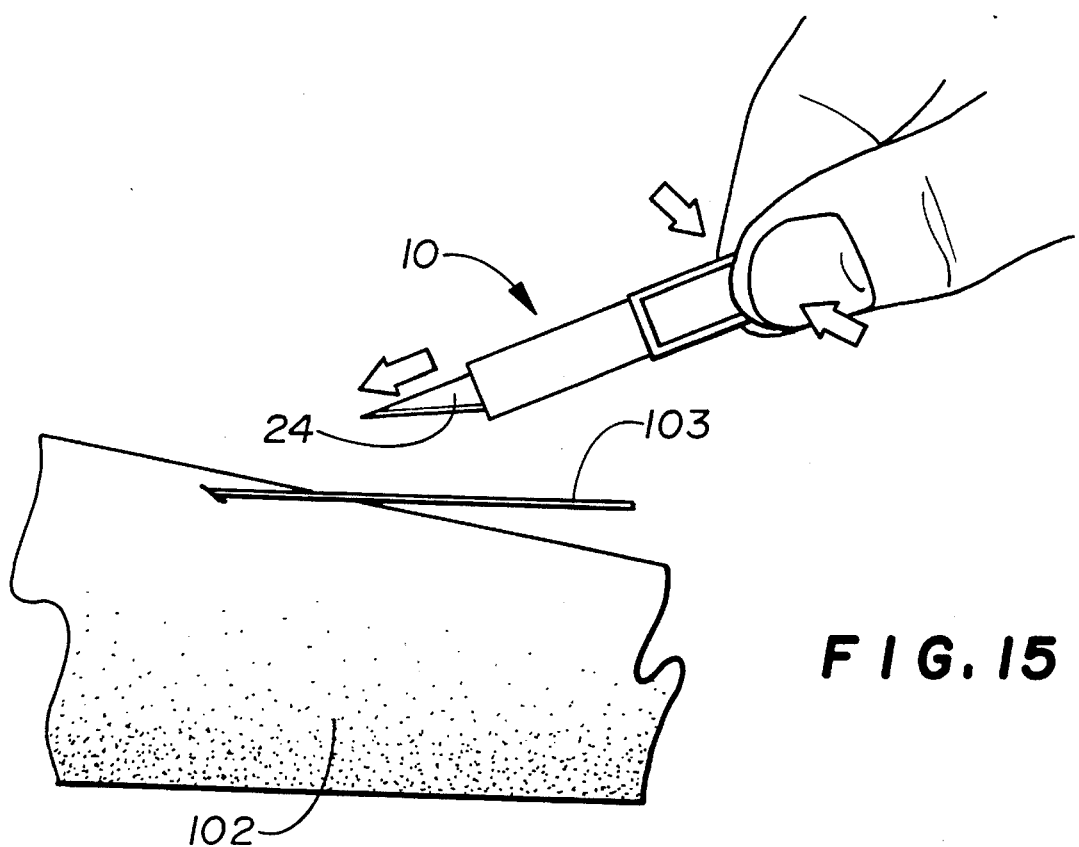
Figure 18:
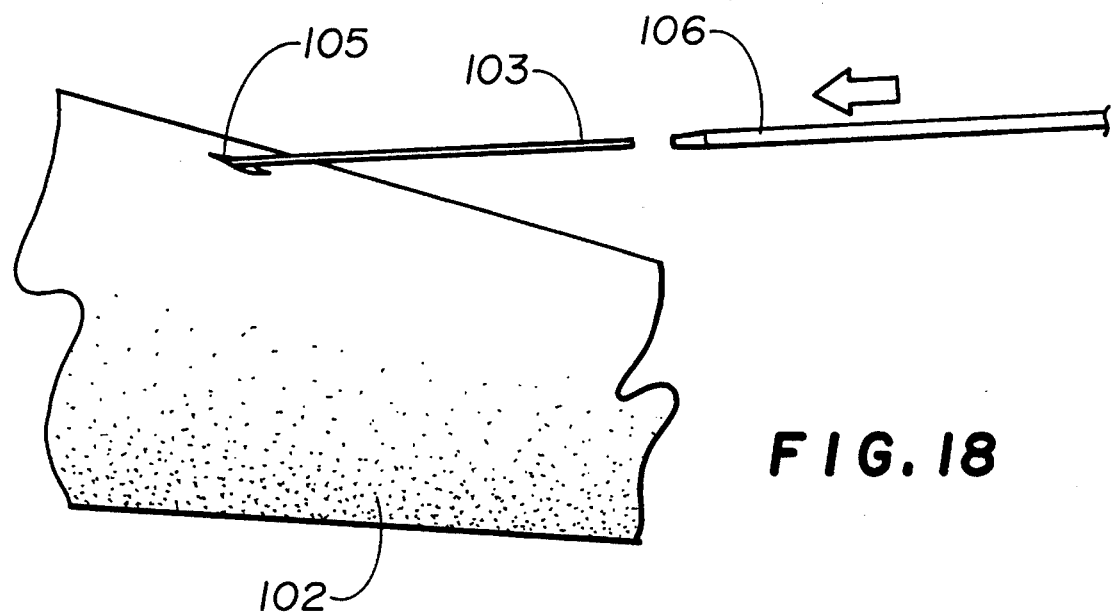
Figure 19:
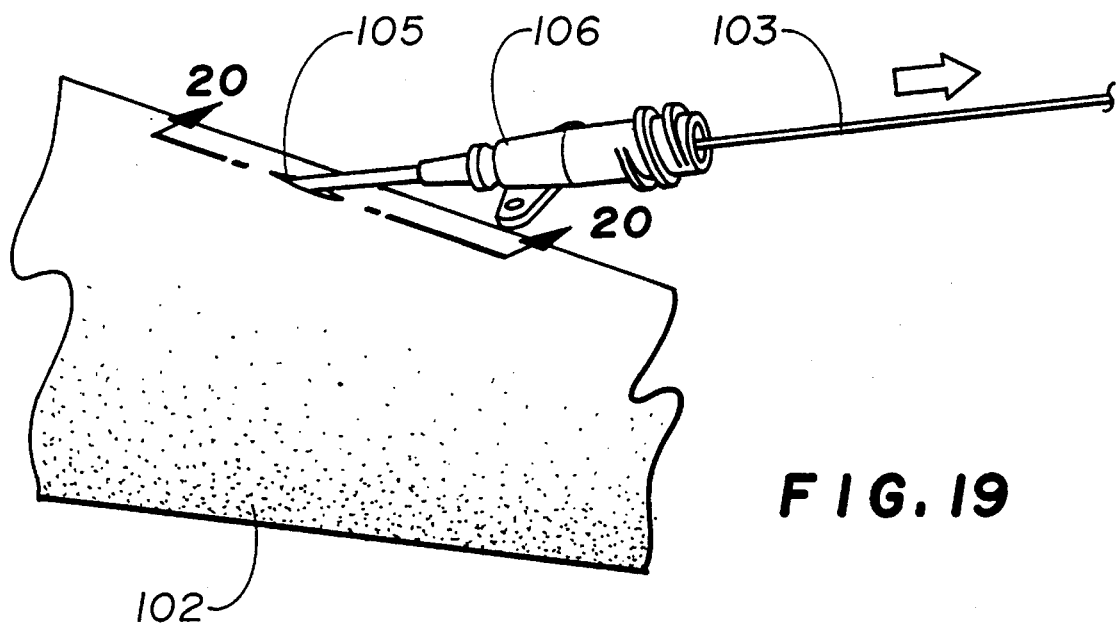

The guarded finger scalpel 10 (or 10') of the present invention is grasped by the surgeon, usually between the surgeon's thumb and forefinger (FIG. 14), and is squeezed to advance the blade 24 (FIG. 15). The blade 24 is then used to make an incision or cut 105 in the patient's skin (FIG. 16). One or more cuts 105 may be made, thereby enlarging the puncture 101 (and facilitating the subsequent insertion of a catheter). Manual pressure is released to retract the blade 24, and the guarded finger scalpel 10 is lifted away from the cut 105.

The blade 24 is no longer exposed, and the guarded finger scalpel 10 is then discarded.

Figure 20:
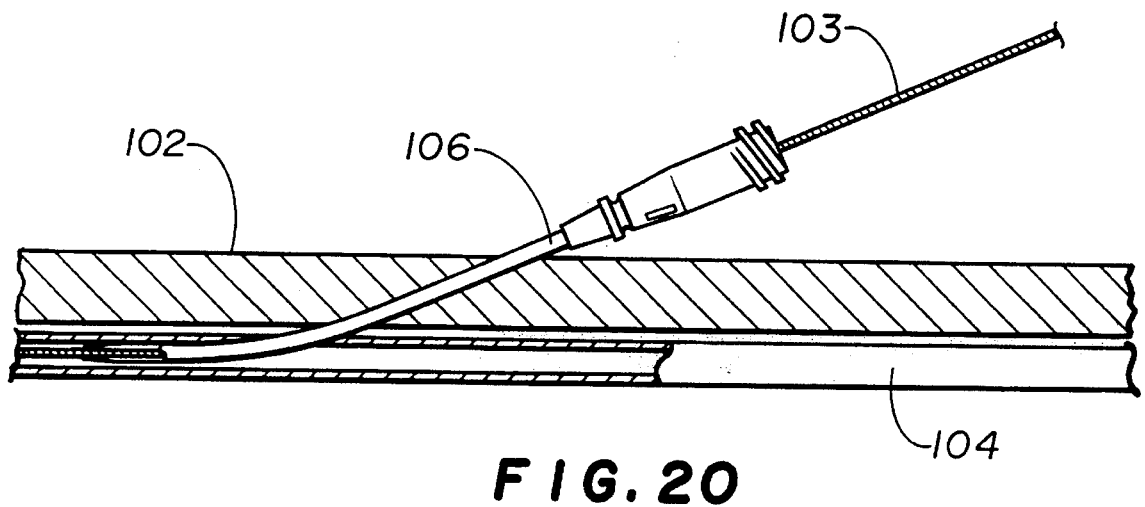
Figure 21:
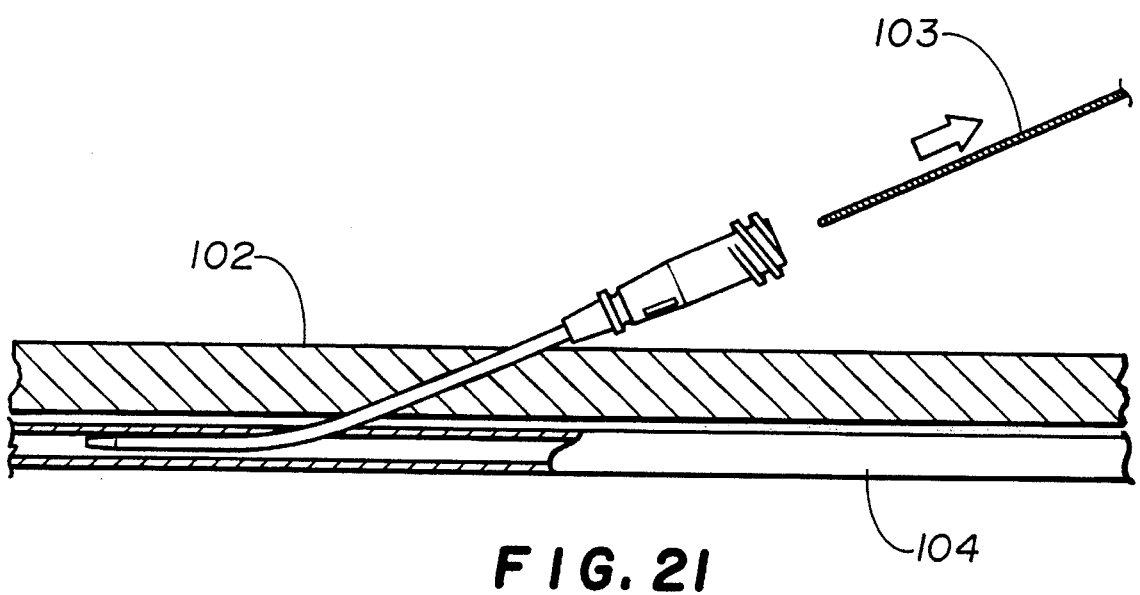

Thereafter, a catheter 106 (FIG. 18) is slipped over the guide wire 103 and through the cut 105 (FIG. 19) and into the patient's vein 104 (FIG. 20). Once the catheter 106 is in place, or while the catheter 106 is being inserted, the guide wire 103 is removed (as shown in FIG. 21).

Figure 22:
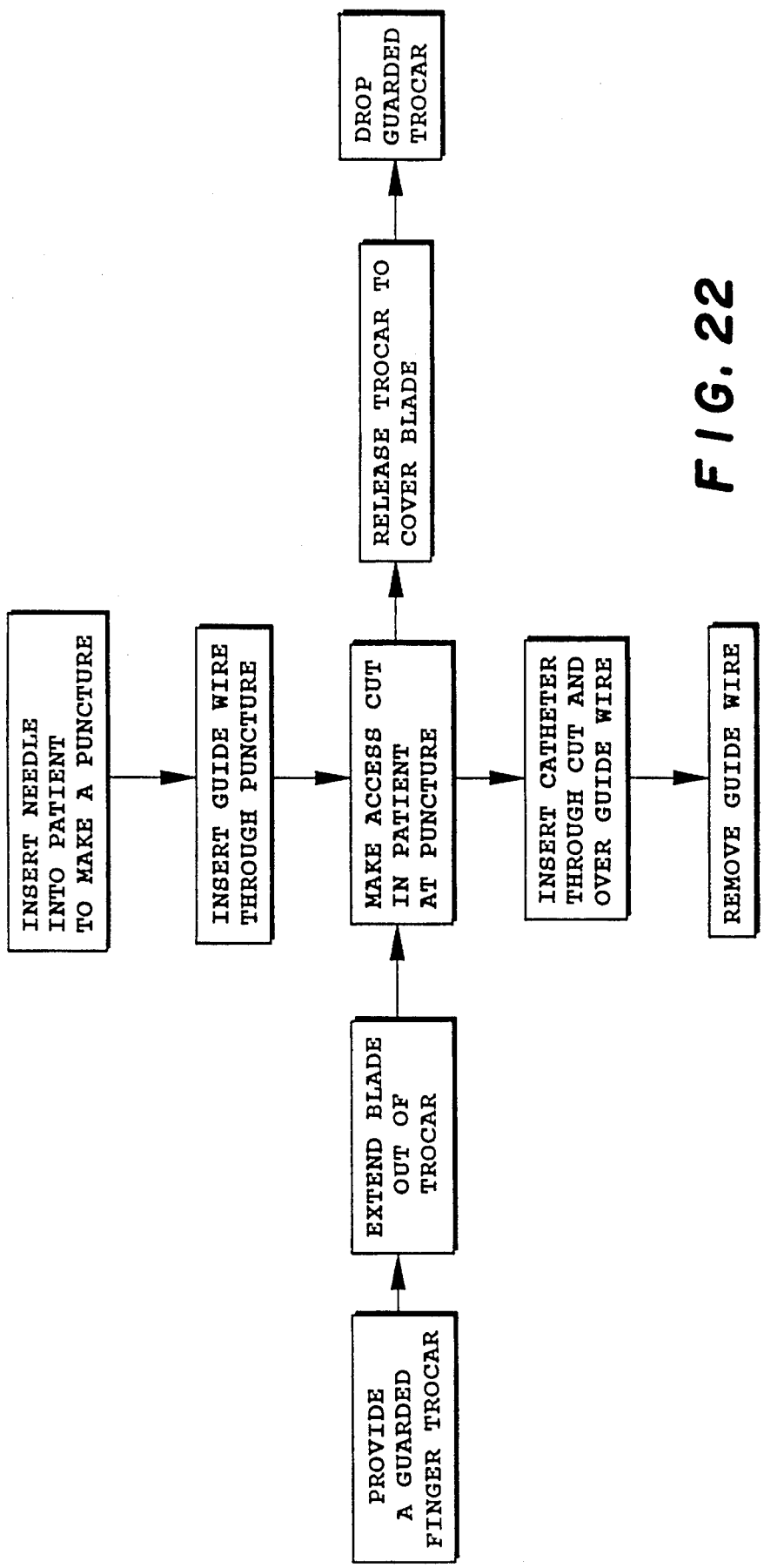
FIG. 22 is a schematic block diagram showing the preferred method of using the guarded finger scalpel of the present invention.
Figure 25:
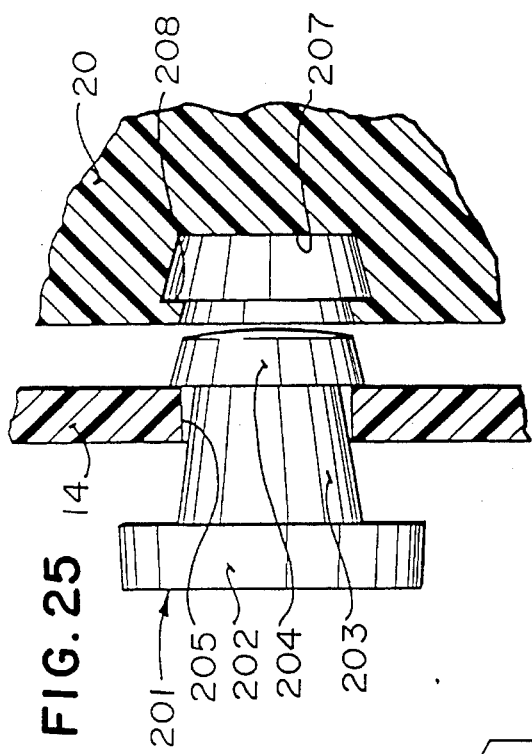
FIG. 25 is a cross-sectional view thereof, taken along the lines 25—25 of FIG. 24 and drawn to an enlarged scale, and showing the pocket formed within the inner member.

This sequence of steps of the preferred method of using the guarded finger scalpels 10 and 10' of the present invention is illustrated in the schematic block diagram of FIG. 22.

With reference to FIGS. 23–28, the guarded finger scalpel 10 is provided with a lock-off means 200. In this embodiment, the lock-off means 200 includes a lock-off button 201 carried by a side portion or wall 14 of the guarded finger scalpel 10. This lock-off button 201, as shown more clearly in FIG. 25, includes an enlarged head 202, a tapered body 203, and an enlarged foot 204, all of which, if desired, may be molded from a suitable plastic material. The lock-off button 201 may be pushed through a hole 205 in the side wall 14 and loosely retained therein between the enlarged head 202 and the enlarged foot 204. The enlarged head 202 may be roughened or knurled, as at 206 in FIG. 24, to facilitate a convenient manipulation thereof.

The forward portion 20 of the inner member (comprising the respective spring arms 18 and 19) has a blind pocket 207 formed therein. This blind pocket 207 is preferably tapered inwardly thereof and has an internal annular shelf 208 formed therein, as shown more clearly in FIG. 25.

Figure 26:
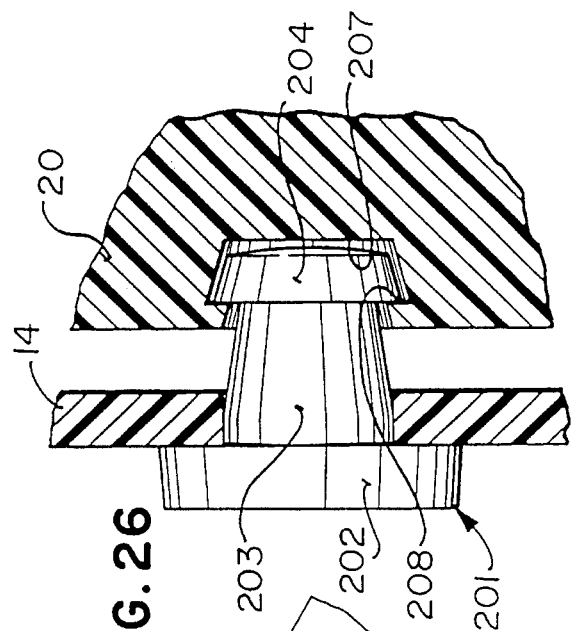
FIG. 26 is a further cross-sectional view, corresponding substantially to FIG. 25, but showing the lock-off button pushed inwardly and received within the pocket formed in the inner member, thereby locking the inner member and hence the blade in its retracted position.
Figure 23:
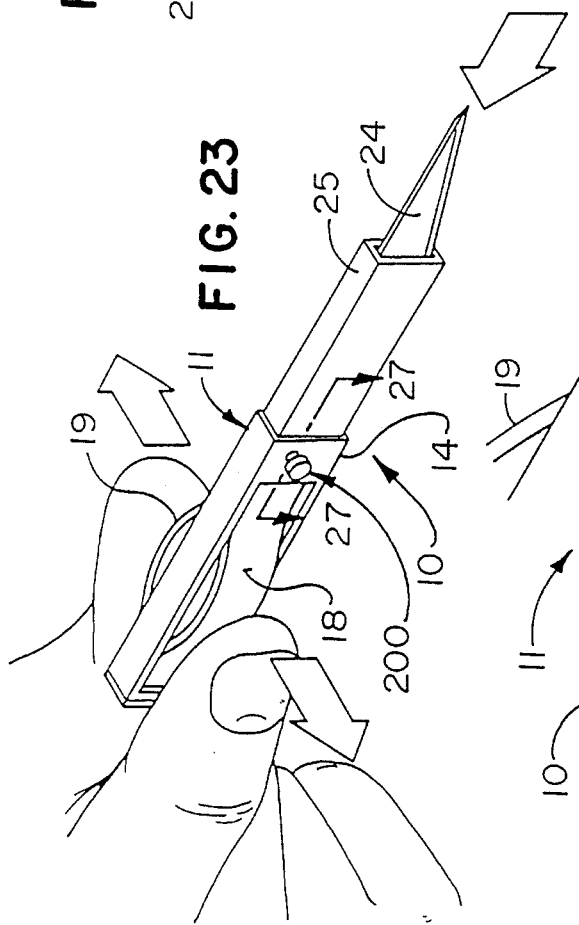
FIG. 23 is a perspective view of a further embodiment of the present invention, wherein a lock-off means is provided to lock the blade in its retracted position and prevent further movement of the blade relative to the guard on the frame.
Figure 24:
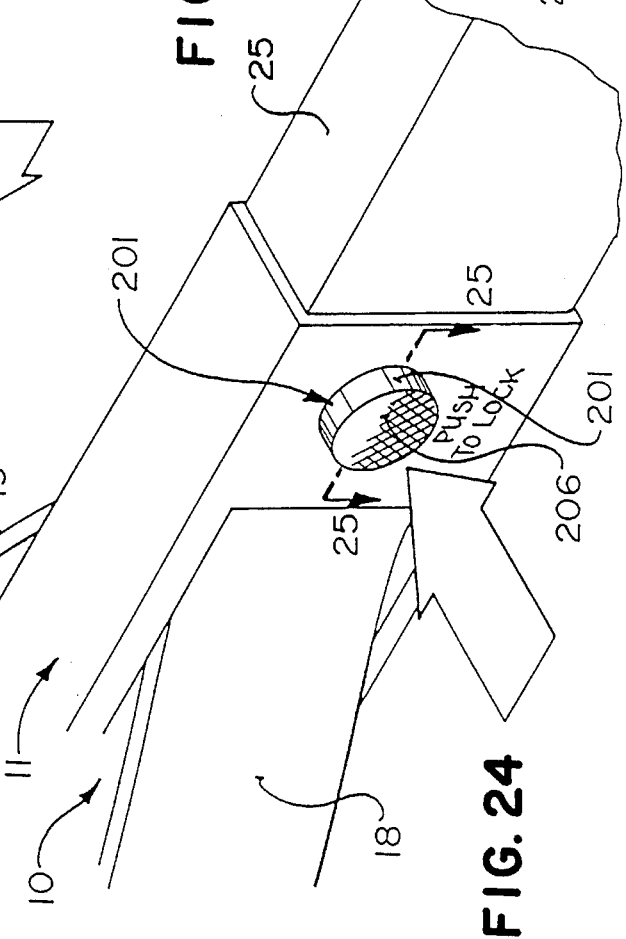
FIG. 24 is a portion of FIG. 23, drawn to an enlarged scale, and showing a lock-off button on the frame.

When the surgical procedure of installing a line in a patient has been completed, and no further use of the guarded finger scalpel 10 is required, the lock-off button 201 may be pushed inwardly thereof (FIG. 24) so that its enlarged foot 204 is "popped" into the blind pocket 207 and is received firmly therein, as shown more clearly in FIG. 26. The forward portion 20 of the inner member is thereby locked to the frame 11.

Thereafter, the blade 24 cannot extend beyond the guard 25 even if the respective spring arms 19 and 20 (or one of them) is squeezed inadvertently or accidentally. This feature is very desirable in preventing nicks or cuts to the surgeon, nurse, technician or clean-up personnel while disposing of the guarded finger scalpel 10 and its overall kit. Thus, the guarded finger scalpel 10 of the present invention is provided, not only with a guard for protection while installing a line, trocar or similar medical device in a patient, but is also provided with the lock-off means 200 for protection during disposal and clean-up.

Figure 29:
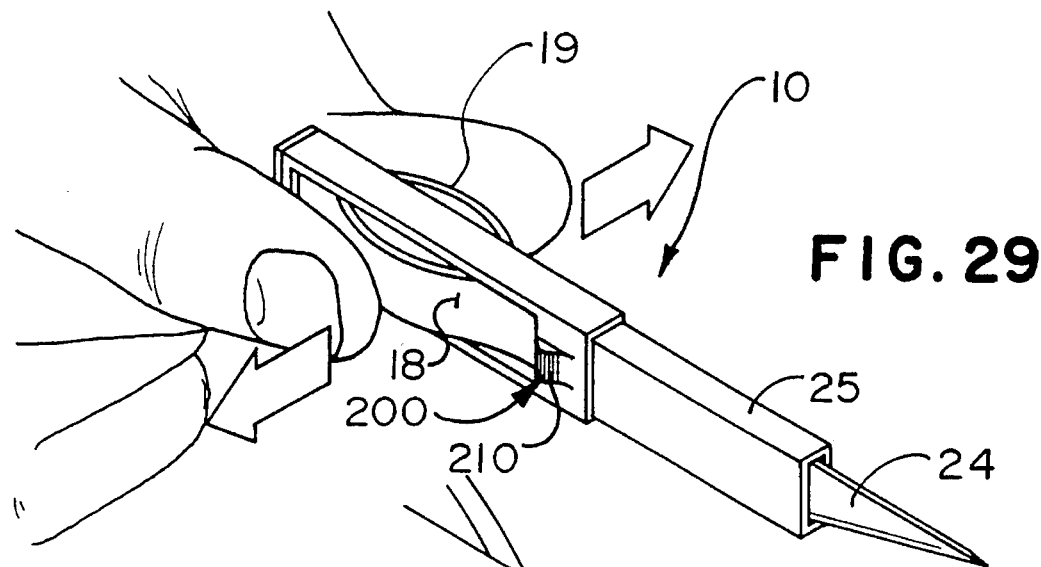
FIG. 29 is a perspective view of a further embodiment, whereby the lock-off button is carried by a depressible tang formed on a side wall of the frame.
Figure 30:
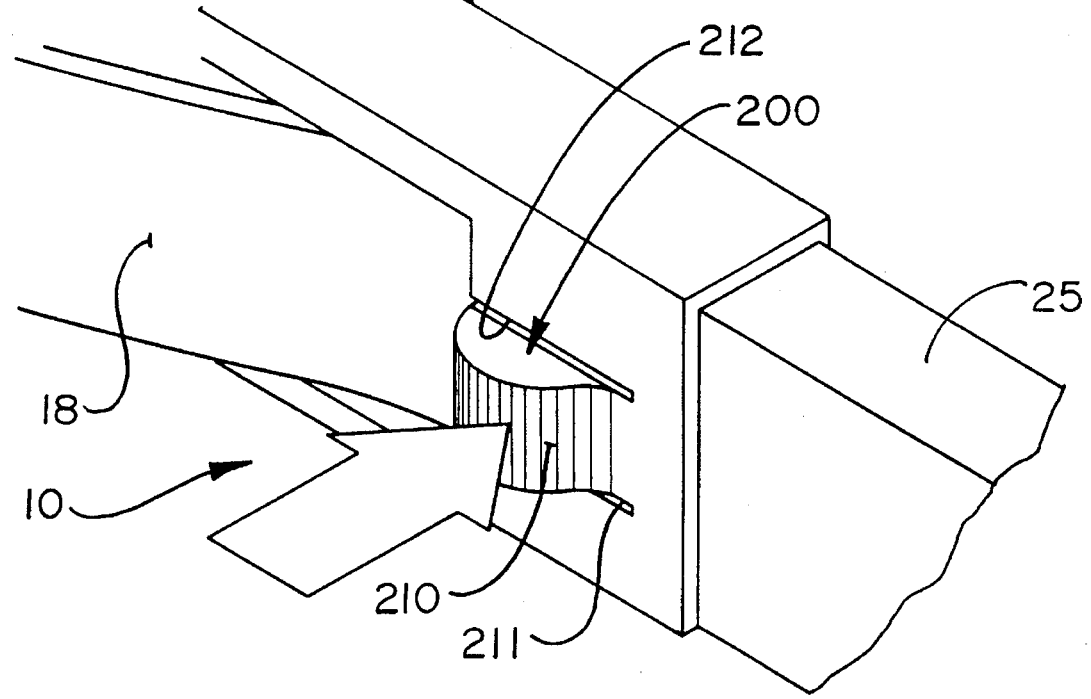
FIG. 30 is an enlarged portion of FIG. 29, showing the lock-off button on the disposable tang being pushed inwardly of the frame and into the locking position thereof.

With reference to FIGS. 29 and 30, a lock-off button 209 may be molded integrally with a depressible tang 210 formed by a pair of parallel slots 211 and 212, respectively, in the side wall 14 of the guarded finger scalpel 10.

Obviously, many modifications may be made without departing from the basic spirit of the present invention. For example, instead of the patient's vein (as shown herein) the flexible guide wire 103 may be inserted into a patient's organ, vessel or body cavity under certain circumstances during a surgical procedure. Also, the guarded finger scalpel may be used by any health care provider, such as a cardiologist, pulmonary doctor, anesthesiologist, nurse, etc. Accordingly, it will be appreciated by those skilled in the art that within the scope of the appended claims, the invention may be practiced other than has been specifically described herein.

What is claimed is:

1. A disposable guarded finger scalpel, wherein the disposable guarded finger scalpel is used while inserting a line in a patient, comprising a frame normally grasped between a thumb and forefinger, the frame including a blade guard forwardly thereof and having an opening therein, an inner member nested within the frame and including at least one spring arm disposed rearwardly of the frame and extending laterally therefrom, the inner member including a forward portion having a longitudinal lug formed thereon, a blade having a longitudinal slot receiving the lug on the forward portion of the inner member, thereby mounting the blade on the inner member, the blade normally being retracted within the blade guard, the inner member having a cap means rearwardly thereof, and the frame having a rear end wall abutting against the cap means on the inner member, thereby securing the inner member within the frame, wherein the at least one spring arm is manually squeezed laterally inwardly of the frame, thereby advancing the blade outwardly through the opening in the blade guard and thereby automatically retracting the blade within the guard when the at least one spring arm is manually released, and means for locking the blade in a retracted position of the blade on the frame.

2. The disposable guarded finger scalpel of claim 1, wherein the frame is substantially rectangular, the frame having top and bottom walls, the frame further having side portions with respective openings formed therein, and wherein the at least one spring arm of the inner member comprises a pair of spring arms extending laterally through the openings, respectively, and confined by the top and bottom walls of the frame.

3. The disposable guarded finger scalpel of claim 2, wherein the blade guard is transparent, such that the blade is visible within the guard.

4. The disposable guarded finger scalpel of claim 2, wherein the spring arms are grasped between the thumb and forefinger, and wherein the spring arms have side walls provided with respective roughened portions to accommodate the thumb and forefinger, respectively.

5. A disposable guarded finger scalpel, comprising a generally rectangular frame having top and bottom walls and respective side walls, each of the side walls being provided with an opening formed therein, the frame having a transparent forward portion providing a blade guard, a blade slidably guided within the guard, the blade having a respective side portion provided with a longitudinally-extending slot, an inner member received within the frame and including a forward portion provided with a longitudinal rib received within the longitudinally-extending slot on the blade, and the inner member including a pair of spring arms formed integrally with the forward portion of the inner member and extending through the respective openings in the side walls of the frame laterally thereof, the spring arms being disposed rearwardly on the frame, and the frame having a rear end wall means cooperating with a cap means on the spring arms, thereby longitudinally securing the spring arms within the frame, such that the spring arms may be squeezed laterally together and inwardly of the frame, thereby advancing the blade forwardly of the transparent blade guard, and such that when the spring arms are released, the blade is automatically retracted within the transparent guard, and means for locking the blade in a retracted position of the blade on the frame.

6. In the method of inserting a line in a patient, wherein a needle is used to make a puncture in the patient's skin, such that a guide wire may be inserted through the needle and the puncture and into the patient, the needle being removed, and such that a catheter may be inserted subsequently over the guide wire and into the patient, the wire being removed when the catheter is installed, the improvement comprising the steps of providing a disposable guarded finger scalpel including a frame having a transparent blade guard forwardly thereof and having a rearward portion, an inner member nested within the frame and including at least one spring arm disposed rearwardly of the frame and extending laterally therefrom, the inner member including a forward portion having a blade mounted thereon, the blade normally being retracted within the guard, the inner member further including a cap means rearwardly thereof, and the frame having a rear end wall abutting against the cap means on the inner member, thereby securing the inner member within the frame, manually grasping the rearward portion of the frame of the disposable guarded finger scalpel, viewing the blade within the transparent guard, and depressing the at least one spring arm laterally inwardly of the frame, thereby advancing the blade out of the guard, making a cut in the patient's skin substantially at the puncture before the catheter is inserted over the guide wire, thereby facilitating insertion of the catheter, and releasing the at least one spring arm laterally outwardly of the frame, thereby automatically retracting the blade within the transparent guard of the disposable guarded finger scalpel, further including the step of providing a lock-off means on the frame and moving the lock-off means into a locked position to preclude movement of the blade relative to the guard.

7. A disposable kit for installing a line in a patient, the kit including a needle for making a puncture in the patient's skin and further including a catheter and a guide wire therefor, and a guarded finger scalpel in the kit, the guarded finger scalpel comprising an outer frame, an inner member nested within the frame, slidably guided therein for longitudinal movement relative to the frame, and including at least one integrally-formed spring arm extending laterally therefrom, the inner member further including a forwardly-extending portion having a longitudinal lug formed thereon, a blade having a longitudinal slot receiving the lug on the forwardly-extending portion of the inner member, thereby mounting the blade thereon, the frame having a rear end wall, and the inner member having a cap means secured to the rear end wall of the frame, thereby confining the inner member within the frame, and a guard on the frame forwardly thereof and substantially enclosing the blade, such that when the spring arm is squeezed between the thumb and forefinger, the spring arm is depressed into the frame, thereby extending the inner member forwardly of the frame so that the blade extends beyond the guard on the frame, such that the blade on the guarded finger scalpel may be used to enlarge the puncture in the patient's skin, thereby facilitating insertion of the catheter into the patient, and such that upon release of the thumb and forefinger, the spring arm extends laterally of the frame and the blade is retracted within the guard on the frame, thereby protecting the respective health care providers in installing the line in the patient and in cleaning up and subsequent disposal of the kit including the guarded finger scalpel therein, and further including means for locking the blade in a retracted position of the blade.

8. In a finger scalpel for use by a surgeon in installing a line in a patient in a hospital, wherein the finger scalpel is part of a disposable kit, and wherein the finger scalpel includes a body normally intended to be grasped between the surgeon's thumb and forefinger, the body having a blade mounted thereon, the improvement comprising a guard on the body, the guard having a normal position covering the blade and preventing accidental contact therewith, resilient means maintaining the guard in the normal position thereof, such that the resilient means may be manually opposed as the finger scalpel is grasped by the surgeon, thereby exposing the blade relative to the guard, and lock-off means independent of the resilient means, operative in the normal position of the guard and preventing blade exposure, such that the clean-up personnel in the hospital are protected against nicks or cuts during disposal of the kit.

9. The improvement of claim 8, wherein the body comprises a frame including a pair of side walls having respective openings therein, wherein an inner member is confined within the frame and is guided for slidable movement therein, the inner member carrying the blade thereon, and wherein the resilient means comprises a pair of spring arms carried by the inner member, each spring arm extending laterally through a respective opening in the side walls of the frame.

10. In a finger scalpel for use by a surgeon in installing a line in a patient in a hospital, wherein the finger scalpel is part of a disposable kit, and wherein the finger scalpel includes a body normally intended to be grasped between the surgeon's thumb and forefinger, the body having a blade mounted thereon, the improvement comprising a guard on the body, the guard having a normal position covering the blade and preventing accidental contact therewith, resilient means maintaining the guard in the normal position thereof, such that the resilient means may be manually opposed as the finger scalpel is grasped by the surgeon, thereby exposing the blade relative to the guard, and lock-off means independent of the resilient means, operative in the normal position of the guard and preventing blade exposure, such that the clean-up personnel in the hospital are protected against nicks or cuts during disposal of the kit, wherein the body comprises a frame including a pair of side walls having respective openings therein, wherein an inner member is confined within the frame and is guided for slidable movement therein, the inner member carrying the blade thereon, and wherein the resilient means comprises a pair of spring arms carried by the inner member, each spring arm extending laterally through a respective opening in the side walls of the frame, wherein the lock-off means comprises a lock-off button carried transversely by one of the side walls of the frame, and the inner member within the frame having a pocket formed therein, such that the lock-off button may be pushed inwardly of the frame and received within the pocket in the inner member, thereby locking the inner member to the frame and preventing relative sliding movement therebetween.

11. The improvement of claim 10, wherein the lock-off button is carried on a depressible tang formed on the one side wall of the frame.

12. In the method of inserting a line in a patient, wherein a needle is used to make a puncture in the patient's skin, such that a guide wire may be inserted through the needle and the puncture and into the patient, the needle being removed, and such that a catheter may be inserted subsequently over the guide wire and into the patient, the wire being removed when the catheter is installed, the improvement comprising the steps of providing a disposable guarded finger scalpel including a frame having a blade guard forwardly thereof and having a rearward portion, an inner member nested within the frame and including at least one spring arm disposed rearwardly of the frame and extending laterally therefrom, the inner member including a forward portion having a blade mounted thereon, the blade normally being retracted within the guard, providing a lock-off means, manually grasping the rearward portion of the frame of the disposable guarded finger scalpel, depressing the at least one spring arm laterally inwardly of the frame, thereby advancing the blade out of the guard, making a cut in the patient's skin substantially at the puncture before the catheter is inserted over the guide wire, thereby facilitating insertion of the catheter, releasing the at least one spring arm laterally outwardly of the frame, thereby automatically retracting the blade within the guard of the disposable guarded finger scalpel, and moving the lock-off means into a locked position to prevent movement of the blade relative to the guard.

13. A disposable kit for installing a line in a patient, the kit including a needle for making a puncture in the patient's skin and further including a catheter and a guide wire therefor, and a guarded finger scalpel in the kit, the guarded finger scalpel comprising an outer frame, an inner member nested within the frame, slidably guided therein for longitudinal movement relative to the frame, and including at least one integrally-formed spring arm extending laterally therefrom, the inner member further including a forwardly-extending portion having a lug extending forwardly thereof, a blade having a longitudinal slot receiving the lug on the forwardly-extending portion of the inner member, thereby mounting the blade thereon, a guard on the frame forwardly thereof and substantially enclosing the blade, such that when the spring arm is squeezed between the thumb and forefinger, the spring arm is depressed into the frame, thereby extending the inner member forwardly of the frame so that the blade extends beyond the guard on the frame, such that the blade on the guarded finger scalpel may be used to enlarge the puncture in the patient's skin, thereby facilitating insertion of the catheter into the patient, and such that upon release of the thumb and forefinger, the spring arm extends laterally of the frame and the blade is retracted within the guard on the frame, and further including means for locking the blade in a retracted position of the blade, thereby protecting the respective health care providers in installing the line in the patient and in cleaning up and subsequent disposal of the kit including the guarded finger scalpel therein.

14. In combination, a guarded finger scalpel for use by a surgeon in installing a line in a patient, comprising a body having a blade mounted thereon, a guard on the body, resilient means mounted on the body for maintaining the guard in a position relative to the blade, wherein the blade is covered, wherein the surgeon may grasp the resilient means for exposing the blade, such that the blade has a first covered position and a second exposed position, and locking means maintaining the blade in its covered position, the locking means being independently mounted on the body.

* * * * *

UNITED STATES PATENT AND TRADEMARK OFFICE
CERTIFICATE OF CORRECTION

PATENT NO. : 5,545,175

DATED : August 13, 1996

INVENTOR(S) : Abidin et al.

It is certified that error appears in the above-identified patent and that said Letters Patent is hereby corrected as shown below:

On the title page, item [54], "Quarded" should read -- Guarded --. and
"Patent" should read -- Patient --.
On the title page, item [75], "Micheal" should read -- Michael --.

Signed and Sealed this

Third Day of December, 1996

Attest:

BRUCE LEHMAN

*Attesting Officer*       *Commissioner of Patents and Trademarks*